(12) United States Patent
Hsieh et al.

(10) Patent No.: US 9,198,873 B2
(45) Date of Patent: Dec. 1, 2015

(54) FUNCTIONALIZED NANOPARTICLE, METHOD FOR PREPARING THE SAME AND APPLICATION THEREOF

(75) Inventors: Patrick C. H. Hsieh, Tainan (TW);
Min-Feng Cheng, Kaohsiung (TW);
Chih Han Chang, Tainan (TW);
Wei-Yin Liao, Pingtung County (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 367 days.

(21) Appl. No.: 12/838,933

(22) Filed: Jul. 19, 2010

(65) Prior Publication Data
US 2012/0015037 A1    Jan. 19, 2012

(51) Int. Cl.
*A61K 38/19* (2006.01)
*A61K 9/14* (2006.01)
*A61K 38/00* (2006.01)
*A61K 38/18* (2006.01)
*A61K 38/30* (2006.01)
*A61K 48/00* (2006.01)
*A61K 9/51* (2006.01)
*A61L 27/54* (2006.01)

(52) U.S. Cl.
CPC .............. *A61K 9/5153* (2013.01); *A61K 9/5146* (2013.01); *A61L 27/54* (2013.01); *A61L 2300/252* (2013.01); *A61L 2300/258* (2013.01); *A61L 2300/414* (2013.01); *A61L 2300/426* (2013.01); *A61L 2400/12* (2013.01)

(58) Field of Classification Search
CPC .................................................. A61K 9/5153
See application file for complete search history.

(56) References Cited

U.S. PATENT DOCUMENTS

2013/0101672 A1*    4/2013    Cheng et al. .................. 424/491

OTHER PUBLICATIONS

Zhou et al (Macromolecular Science. Published online Dec. 2008; 9: 326-335).*
Byrne et al (Advanced Drug Delivery Reviews. 2008; 60: 1615-1626).*
Kasturi et al (Journal of Controlled Release. 2006; 113: 261-270).*
Betancourt et al (Journal of Biomedical Materials Research Part A. 2009 (published online Nov. 3, 2008); 91A: 263-276).*
Kim et al. (Langmuir. 2005; 21(19): 8852-8857).*

* cited by examiner

*Primary Examiner* — Scott Long
(74) *Attorney, Agent, or Firm* — Birch, Stewart, Kolasch & Birch, LLP

(57) ABSTRACT

The present invention relates to a new type of functionalized nanoparticles for drug delivery, comprising a type of polymer nanoparticles, a polymer stabilizer coating, and a drug, wherein said polymer stabilizer coating is coated on the surface of said type of polymer nanoparticles, and said drug is conjugated to said polymer stabilizer coating. The present invention also relates to a method for preparing the nanoparticles; and provides a method for treating an ischemic or degenerative disease, comprising administrating an effective amount of the type of functionalized nanoparticles to a subject.

8 Claims, 16 Drawing Sheets
(6 of 16 Drawing Sheet(s) Filed in Color)

(b)

(c)

(a)

(b)

FUNCTIONALIZED NANOPARTICLE, METHOD FOR PREPARING THE SAME AND APPLICATION THEREOF

BACKGROUND OF THE INVENTION

1. Field of the Invention

The present invention relates to a new type of functionalized nanoparticles for drug delivery, the method for preparing the nanoparticles, and applications thereof.

2. Description of the Related Art

Although new approaches for treating cardiac diseases including controlled drug delivery (Engel et al. Proc Natl Acad Sci USA 103, 15546-15551 (2006)) and stem cell therapy (Orlic et al. Nature 410, 701-705 (2001) and Quevedo et al. Proc Natl Acad Sci USA 106, 14022-14027 (2009)) have been suggested, it remains challenged to obtain therapeutic but not side effects. Microsphere (Sy et al. Nat Mater 7, 863-868 (2008)) and gel-like materials (Hsieh et al. J Clin Invest 116, 237-248 (2006) and Davis et al. Proc Natl Acad Sci USA 103, 8155-8160 (2006)) have been reported to be used for delivering drugs, prolonging the drug retention in the infracted area and improving cardiac functions. Although these materials can be used to deliver drugs into the heart, they may not be suitable for controlled drug release as their sustention in the infarcted area is typically too long, leading to poorly characterized release kinetics of drugs. Moreover, it is unclear how these implanted materials can be retained in the infarct area for a long time (typically for weeks or months) without degradation at an appropriate rate (Anderl et al. Journal of Biomedical Materials Research Part A 88A, 704-710 (2009)) which ultimately results in an inflammatory response and/or a foreign body reaction.

SUMMARY OF THE INVENTION

In view of the limitations of the above mentioned conventional technologies, one of the major objectives of the present invention is to provide a novel type of functionalized nanoparticles for drug delivery, particularly, a type of Insulin-like Growth Factor-conjugated poly(D,L-lactide-co-glycolide) nanoparticles (PLGA-IGF-1 NPs), which provide cardioprotection after acute myocardial infarction.

Another objective of the present invention is to provide an easy and simple method for manufacturing this type of PLGA-IGF-1 NPs of the present invention without damaging the functions of IGF-1.

Yet the third objective of the present invention is to provide a method for treating ischemic diseases such as ischemic stroke and peripheral arterial occlusive disease, or degenerative diseases such as musculoskeletal or neurological disorders, comprising administrating an effective amount of this type of functionalized nanoparticles of the present invention to a subject.

In addition, the present invention also provides a method of using this type of functionalized nanoparticles of the present invention for regenerative medicine.

To achieve the above objectives, the present invention provides a new type of functionalized nanoparticles for drug delivery, comprising a type of polymer nanoparticles, a polymer stabilizer coating, and a drug, wherein said polymer stabilizer coating is coated on the surface of said type of polymer nanoparticles, and said drug is conjugated to said polymer stabilizer coating.

In the preferred embodiments, the polymer of said type of polymer nanoparticles is selected from biodegradable polymers or natural materials; more preferably, selected from PLGA, collagen, gelatin, chitosan, chitin, hyaluronic acid, alginate, albumin, fibrin, agarose or cellulose; most preferably, PLGA.

In the preferred embodiments, the type of functionalized nanoparticles have an average diameter of from 5 to 500 nm; more preferably, from 5 to 300 nm; most preferably, from 70 to 80 nm.

In the preferred embodiments, said polymer stabilizer is poly(ethylene)imine, polylysine or a polyamine material selected from the group of spermidine, putrescine and polyethylene glycol; most preferably, poly(ethylene)imine.

In the preferred embodiments, said drug is a cytokine, growth factor, synthetic protein, compound, DNA or RNA for therapy; more preferably, IGF-1, PDGF, VEGF, HGF, G-CSF, FGF, BMP, SHH, periostin, neuregulin, a p38 inhibitor or a combination thereof; most preferably, IGF-1.

In the preferred embodiments, the type of functionalized nanoparticles is administrated by injection; more preferably, by direct myocardial injection through transthoracic surgery, cardiac catheterization or echo-guided approach.

The present invention also provides a method for preparing the above-mentioned type of functionalized nanoparticles, comprising:
(a) providing a polymer solution;
(b) adding an alcohol solution or water into said PLGA solution with stirring to obtain a nanoparticle suspension;
(c) transferring the suspension into a polymer stabilizer solution and homogenizing;
(d) filtering the homogenized suspension from step (c) to obtain a type of polymer stabilizer-coated polymer nanoparticles;
(e) adding said type of polymer stabilizer-coated polymer nanoparticles into a drug solution to obtain the type of functionalized nanoparticles.

In the preferred embodiments, the polymer of said type of polymer nanoparticles is selected from biodegradable polymers or natural materials; more preferably, selected from PLGA, collagen, gelatin, chitosan, chitin, hyaluronic acid, alginate, albumin, fibrin, agarose or cellulose; more preferably, PLGA.

In the preferred embodiments, the type of functionalized nanoparticles have an average diameter of from 5 to 500 nm; more preferably, from 5 to 300 nm; most preferably, from 70 to 80 nm.

In the preferred embodiments, said polymer stabilizer is poly(ethylene)imine, polylysine or a polyamine material selected from the group of spermidine, putrescine and polyethylene glycol; most preferably, poly(ethylene)imine.

In the preferred embodiments, said drug is a cytokine, growth factor, or synthetic protein compound, DNA or RNA for therapy; more preferably, IGF-1, PDGF, VEGF, HGF, G-CSF, FGF, BMP, SHH, periostin, neuregulin, a p38 inhibitor or a combination thereof; most preferably, IGF-1.

In the preferred embodiments, said alcohol solution is an ethanol solution or an equivalent.

Yet the present invention also provides a method for treating an ischemic disease such as ischemic stroke and peripheral arterial occlusive disease, or a degenerative disease such as a neurological or musculoskeletal disorder, comprising administrating an effective amount of the above-mentioned type of functionalized nanoparticles to a subject.

The present invention further provides a method of using the above-mentioned type of functionalized nanoparticles for regenerative medicine.

The type of PLGA-IGF-1 NPs of the present invention has the ability to inhibit doxorubicin-induced cardiomyocyte apoptosis through the activation of Akt phosphorylation in vitro. As for in vivo studies, intramyocardial injection of the type of PLGA-IGF-1 NPs of the present invention results in a longer retention of IGF-1 than injection of IGF-1 alone, and the IGF-1 retention lasts up to at least 24 hours after injection. Furthermore, according to the echocardiography and histology studies, injection of PLGA-IGF-1 NPs into the peri-infarct area of myocardium after infarction prevents cardiomyocyte death, reduces the infarct size and improves cardiac functions of mice. Therefore, the present invention has a potential to be applied in clinical therapies for ischemic heart disease.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE PREFERRED EMBODIMENTS

The inventors designed a nano-sized particle which is smaller than the conventional materials used as drug carriers and degrades at the same rate as the drug loaded thereon. The nano-sized particle of the present invention has several advantages. First, one or more drugs can be carried on one particle because the surface-area/mass ratio of nano-sized particles is higher than that of micro-sized particles. Second, the nano-sized particles diffuse into the tissue, especially heart tissue, effectively. Finally, they can penetrate smaller capillaries and be taken up by cells (see Desai et al. Pharm Res 13, 1838-1845 (1996) and Desai et al. Pharm Res 14, 1568-1573 (1997)).

The examples hereinafter are used to further understand the advantages of the present invention, not used to limit the claims of the invention.

EXAMPLES

Example 1

Preparation of PLGA-IGF-1 NPs of the Present Invention

PLGA powder with the ratio (50/50) of lactide to glycolide (50DGOH-040, M.W. 35,000-65,000 Da, purchased from Bio Invigor Co.) was dissolved in 5 mL of acetone with the final concentration of 10 mg/mL. Then an ethanol solution composed of ethanol/H2O (50/50, % v/v) was added to the PLGA solution dropwise (1 mL/min) by using a tubing pump and stirred at 400 rpm with a magnetic stirrer until turbidity appeared. Following 5 more minutes of stirring, the suspension was transferred into 20 mL of poly(ethylene)imine (branched PEI, purchased from Sigma) in a glass beaker and homogenized at low speed for 20 minutes. The polymer stabilizer is used to increase the stability of the NPs in the present invention, and the $NH_3^+$ group on PEI conjugates with the $COOH^-$ group on IGF-1. Both branched and linear PEIs can be used in the present invention.

Then the homogenized suspension was filtered through a 0.22 μm filtration membrane to obtain PLGA NPs (PLGA nanoparticles), and the PLGA NPs were washed three times with deionized water. After that, an IGF-1 (Pepro Tech) aqueous solution of a specific concentration was added to the PLGA solution at 4° C. for 1 hour, in which the solution was vortexed every ten minutes to give a PLGA-IGF-1 NP solution. The PLGA-IGF-1 NP solution was centrifuged at 14,000 rpm for 20 min and the supernatant was discarded. Then the PLGA-IGF-1 NP was washed by water by centrifugation three times to remove the residual IGF-1.

Figure 1:
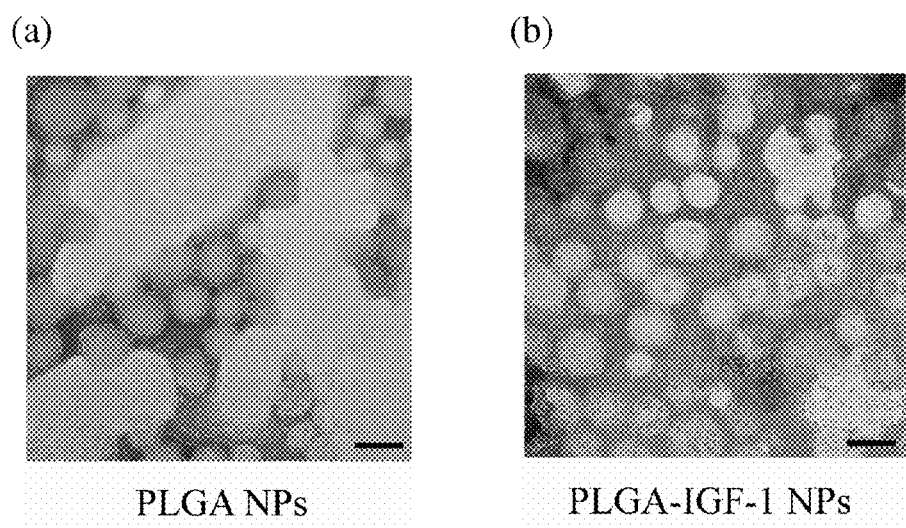
FIG. 1 represents the transmission electron micrograph images of (a) PLGA NPs and (b) PLGA-IGF-1 NPs (scale bar: 100 nm).

Traditionally, polymer stabilizers used to prevent the aggregation PLGA NPs are poly(vinyl alcohol) (PVA), Tween 80 and Fluonic 127 (poloxamer 407) (Jain et al. Biomaterials 21, 2475-2490 (2000) and Kim et al. Langmuir 21, 8852-8857 (2005)). However, these stabilizers may change the zeta potential of PLGA NPs, the particle size as well as the particle surface properties. Most polymer stabilizers do not have functional groups for further modification and their biomedical applications are limited hence. In the present invention, poly(ethylene)imine (PEI) is used as a polymer stabilizer to prevent denature of IGF-1. IGF-1 is negatively charged and is able to bind to the positively charged amino groups of the functionalized PLGA NPs by electrostatic forces. Therefore, no other chemical agent is required. The surface morphologies of PLGA NPs and PLGA-IGF-1 NPs observed by transmission electron microscope (Hitachi 7500) are shown in FIGS. 1a and 1b, and the mean diameter of PLGA NPs and PLGA-IGF-1 NPs are 66.2±15.3 nm and 74.4±11.3 nm, respectively. There is no obvious difference in the surface morphology of PLGA NPs and PLGA-IGF-1 NPs.

In addition, the surface potential of PLGA NPs and PLGA-IGF-1 NPs of the present invention was also determined by zeta potential (Zetasizer 3000HSAdvanced). No obvious difference between both NPs was observed (data not shown).

Example 2

Characterization of PLGA-IGF-1 NPs of the Present Invention

Fourier transform infrared spectroscopy (FTIR) and x-ray photoelectron spectroscopy (XPS), in which the latter one is more sensitive to the former one, were applied to confirm the IGF-1 binding on the surface of PLGA-IGF-1 NPs of the present invention.

Figure 2:
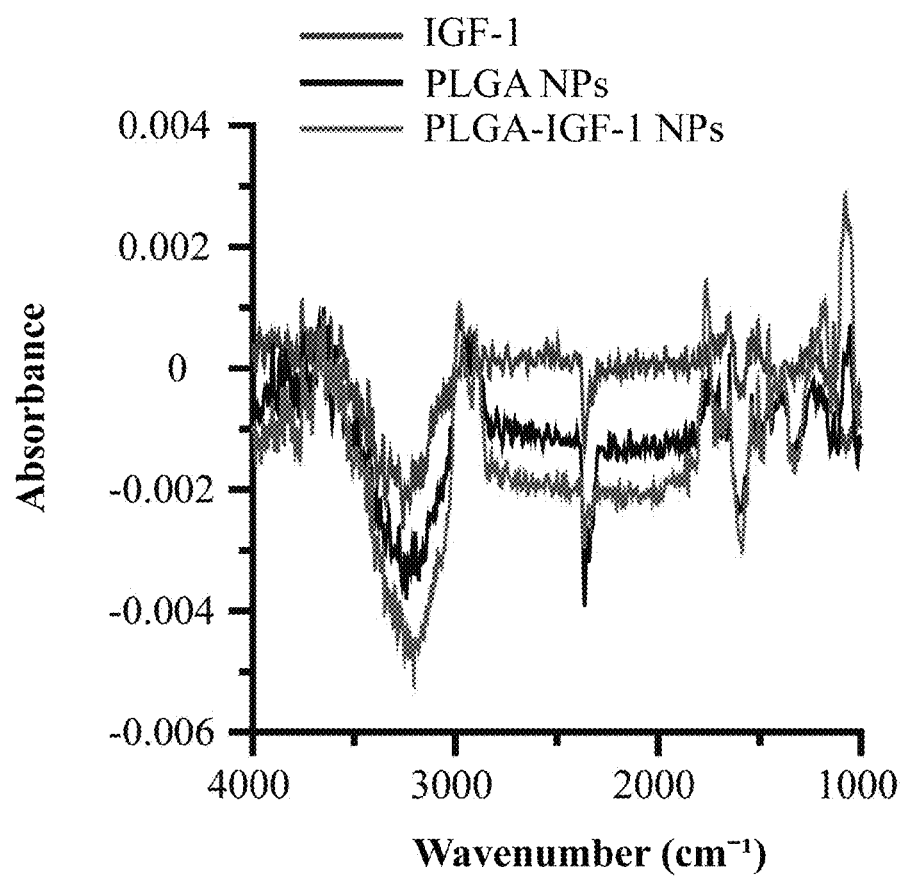
FIG. 2 represents the Fourier transform infrared spectroscopy spectra of IGF-1 (blue), PLGA NPs (black) and PLGA-IGF-1 NPs of the present invention (green).

The surface elements of IGF-1, PLGA NPs and PLGA-IGF-1 NPs of the present invention were determined by FTIR with 500 mm rowland circle Al monochromatic source for excitation. As shown in FIG. 2, the peaks at 3000-3300 cm$^{-1}$ correspond to hydroxyl (—OH) and carboxyl (—COOH). The intensity of the stretch absorption at 3000-3300 cm$^{-1}$ is higher in PLGA-IGF-1 NPs of the present invention than that in PLGA NPs or IGF-1 alone.

Figure 3:
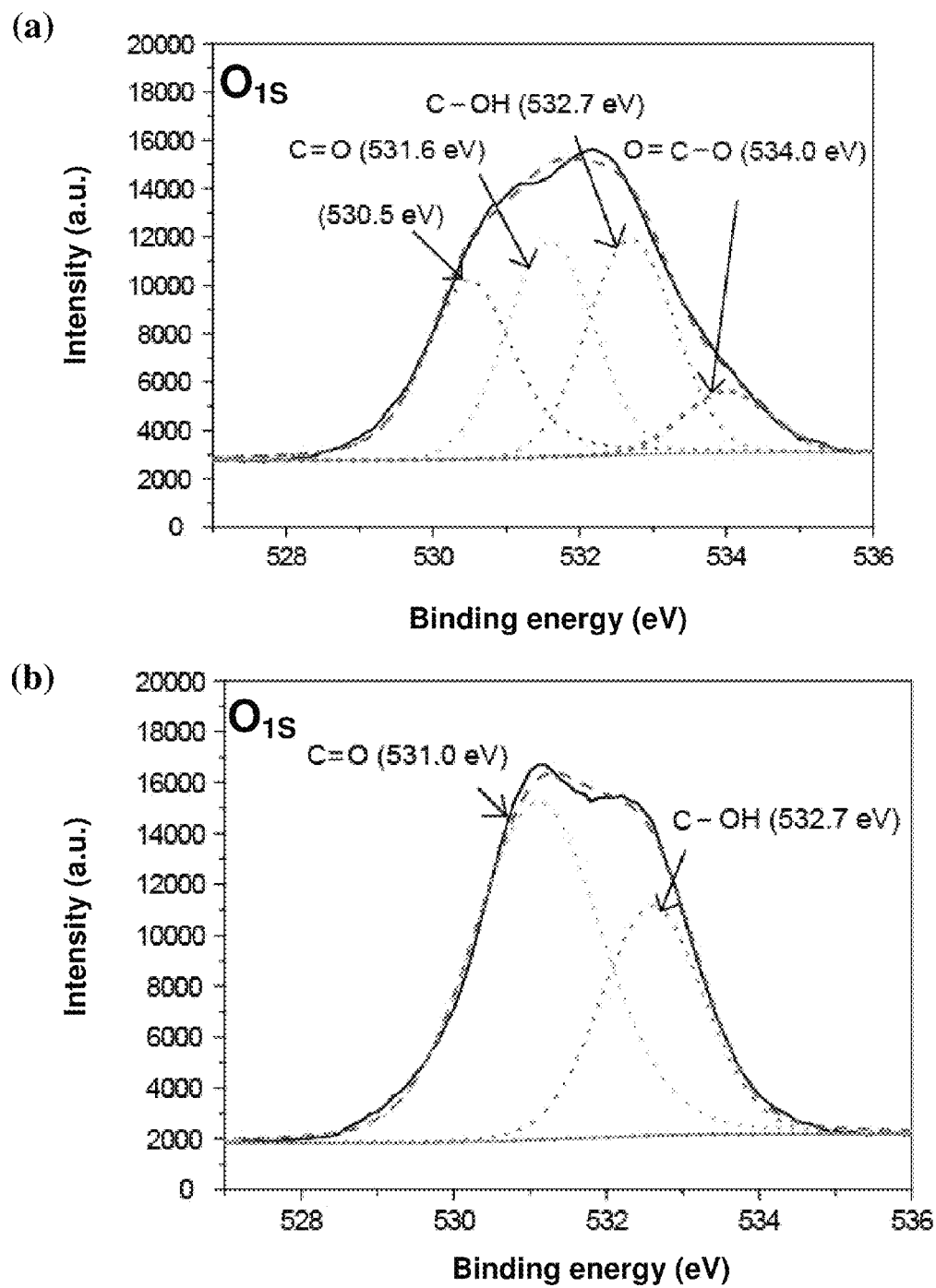
FIG. 3 represents the x-ray photoelectron spectroscopy of (a) PLGA NPs and (b) PLGA-IGF-1 NPs. Black curve: raw data. Red dashed curve: fitting data.

In addition to FTIR, XPS was also used to analyze the chemical composition and chemical state of the surfaces of these nonoparticles by X-ray photoelectron spectroscopy (Kratos Axis Ultra DLD) with 500 mm rowland circle Al monochromatic source for excitation. The XPS results of PLGA NPs and PLGA-IGF-1 NPs of the present invention are shown in FIGS. 3a and 3b, respectively. The peak corresponding to O1s are decomposed in four peaks located at 530.5, 531.6, 532.7 and 534.0 (see Rjeb, M. Contribution to the study by x-ray photoelectron spectroscopy of the natural aging of the polypropylene. The Moroccan Statistical and Condensed Matter Society 5 (2004)). As shown in FIG. 3, the intensity of the peak associated with C=O bond is higher in PLGA-IGF-1 NPs than that in PLGA NPs. PLGA-IGF-1 NPs of the present invention do not comprise $O_{1s}$ located at 530.5.

Further, the element ratio of PLGA NPs and PLGA-IGF-1 NPs of the present invention were calculated in accordance with FIG. 3 using XPSPEAK4.1 software. As shown in FIG. 3, the black curve and red dashed curve indicate raw data and fitting data, respectively. As shown in Table 1, the O/C and N/C of PLGA-IGF-1 NPs are higher than that of PLGA NPs. This indicates that IGF-1 has bound to the surface of PLGA-IGF-1 NPs of the present invention because IGF-1 is a protein, which is composed of amino acids comprising lots of $NH_2$ and COOH groups.

TABLE 1

| | Element ratio (%) | |
|---|---|---|
| | O/C | N/C |
| PLGA NPs | 0.859 | 0.146 |
| PLGA-IGF-1 NPs | 1.07 | 0.186 |

Example 3

IGF-1 Concentration of PLGA-IGF-1 NP of the Present Invention

Figure 4:
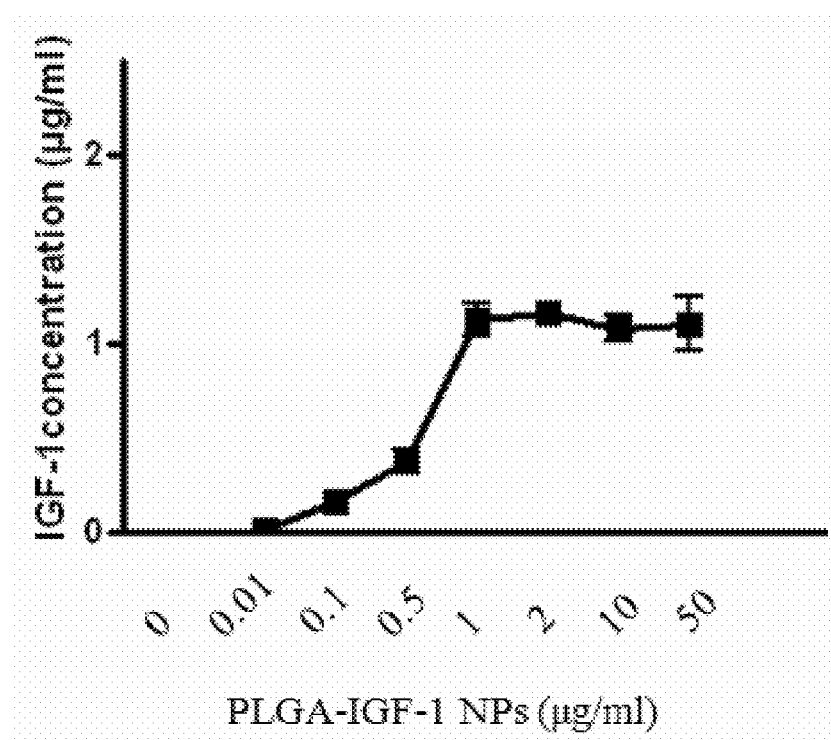
FIG. 4 represents the amount of IGF-1 conjugated on the PLGA-IGF-1 NPs of the present invention determined by ELISA.

A human specific IGF-1 ELISA kit (Diagnostic Systems Laboratories, Webster, Tex.) was used to examine the maximum amount of IGF-1 bound to the surface of PLGA-IGF-1 NPs of the present invention. First, 5 mg/mL of PLGA NPs incubated with different concentrations of IGF-1 ranging from 0.01 μg/mL to 50 μg/mL. Following incubation, unbound IGF-1 was removed by centrifugation. ELISA was proceeded following the manufacturer's instructions. The result shown in FIG. 4 indicates that the maximum amount of IGF-1 conjugated on PLGA-IGF-1 NPs of the present invention is 1 μg/mL.

Example 4

PLGA-IGF-1 NPs of the Present Invention Prolong Akt Phosphorylation of Cardiomyocytes In Vitro The cardiomyocytes used hereinafter were extracted from 1- to 3-day-old Sprague-Dawley rats. All animal protocols were approved by the Institutional Animal Care and Use Committee (IACUC) at National Cheng Kung University.

First, neonatal cardiomyocytes were isolated from Sprague-Dawley rats, and digested with 1 mg/mL trypsin (Sigma) in MSS (GIBIO/BRL) at 4° C. for 3 hrs and then further digested with 0.8 mg/mL collagenase (Type II, Worthington Biochemical Corporation, Lakewood, N.J., USA) in HBSS buffer at 37° C. The isolated cells comprising fibroblasts and cardiomyocytes were collected by centrifugation at 1000 rpm and pre-plated in culture dishes twice, each for 30 minutes, to allow fibroblasts to attach. After fibroblasts were removed, unattached cells, i.e. cardiomyocytes, were seeded on culture dish coated with 1% gelatin (J. T. Baker) and ready for use.

In order to study the dose effect of IGF-1 present in PLGA-IGF-1 NP, each of the IGF-1 solutions with concentrations ranging from 0.01 μg/mL to 50 μg/mL was incubated with a fixed concentration of PLGA NPs (5 mg/ml) to obtain PLGA-IGF-1 NPs with different IGF-1 concentrations, which were used to treat the isolated neonatal cardiomyocytes.

After treatment, the protein extract of the treated cells was collected as well as incubated with an anti-phospho-Akt antibody (1:1000 dilution) or anti-total Akt antibody (1:1000 dilution) (both purchased from Cell Signaling) overnight at 4° C., and then with the corresponding secondary antibodies in 1:25000 and 1:50000 dilutions, respectively. Then the signals were detected by enhanced chemoilluminescence detection kit (Millipore).

Figure 5:
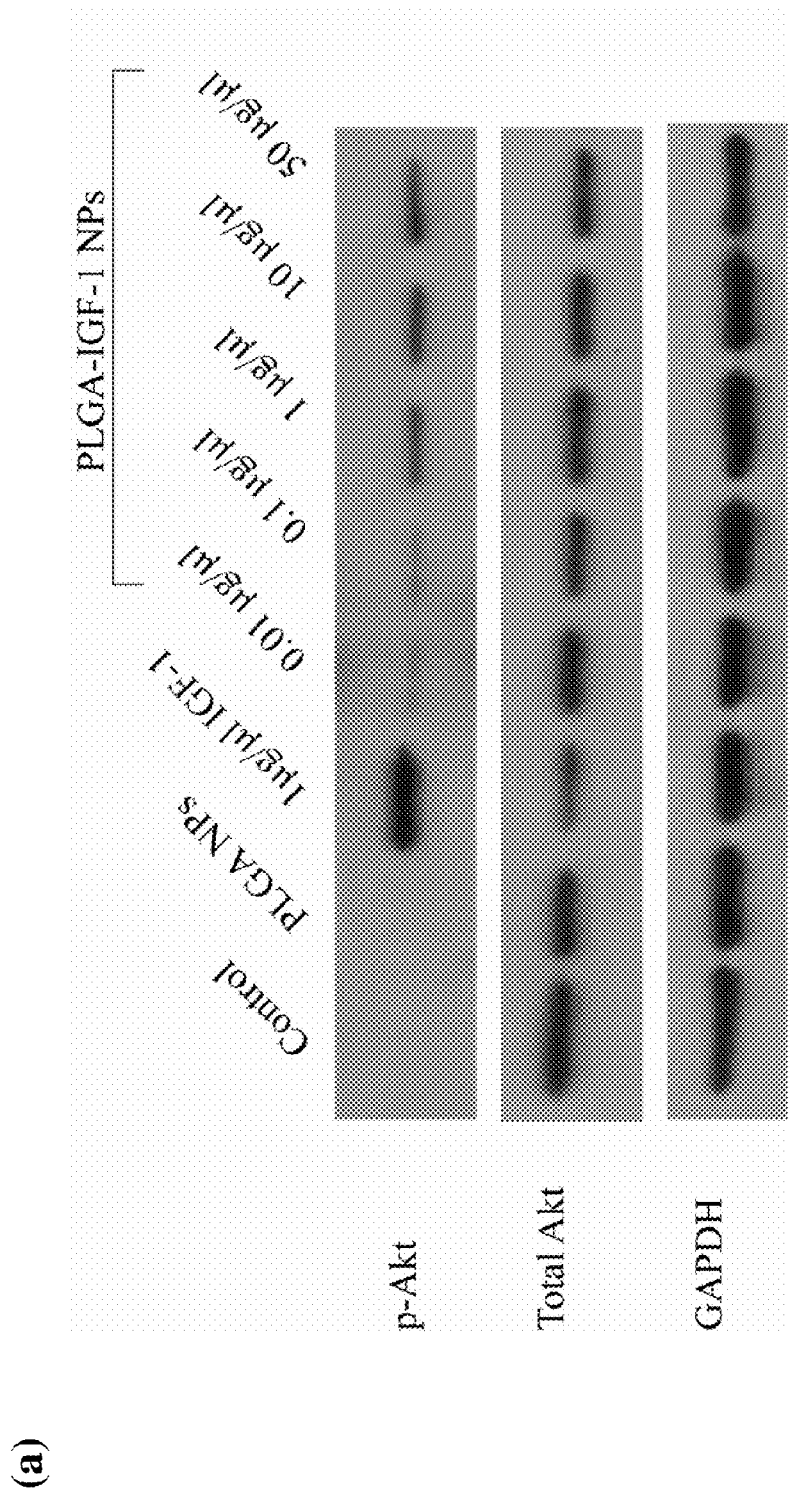
FIG. 5 represents (a) dose effect of PLGA-IGF-1 NPs of the present invention on phosphorylated-Akt (p-Akt), total Akt and GAPDH (internal control) and time effect of (b) IGF-1 (1 μg/mL) and (c) PLGA-IGF-1 NPs of the present invention (1 μg/mL) on Akt phosphorylation.
Figure 5:
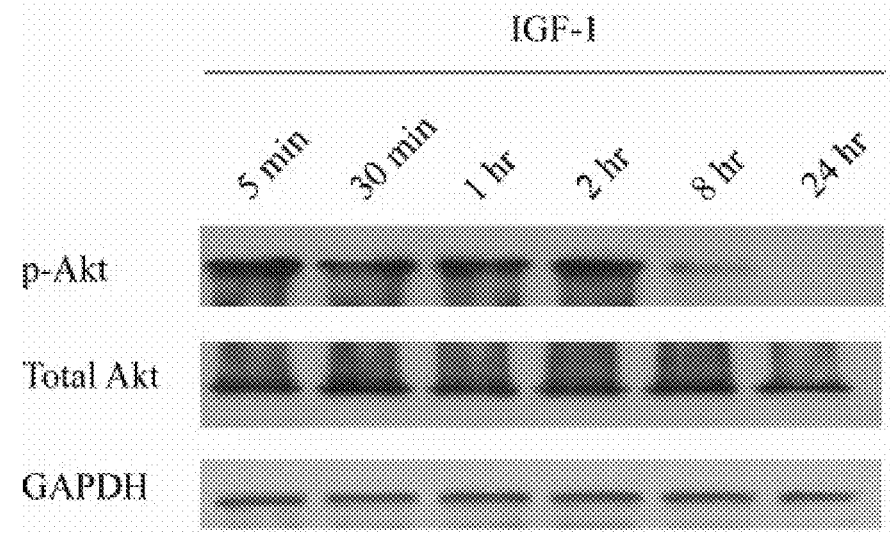
Figure 5:
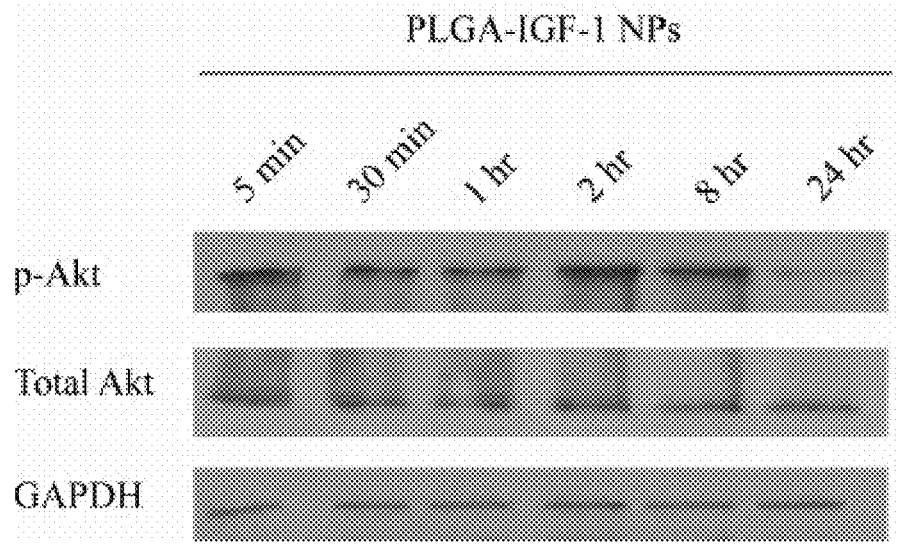

FIG. 5a demonstrates the result of treating cardiomyocytes with IGF-1 alone or PLGA-IGF-1 NPs with a variety of IGF-1 concentrations for 30 minutes, in which IGF-1 alone and PLGA-IGF-1 NPs with a variety of IGF-1 concentrations increase Akt phosphorylation. FIGS. 5b and 5c further demonstrate that IGF-1 alone (1 μg/μL) is able to maintain phosphorylated Akt up to 8 hours, and PLGA-IGF-1 NPs, which conjugate the same concentration of IGF-1 (1 μg/μL) effectively prolong the Akt phosphorylation up to 24 hours. That is to say, the treatment with PLGA-IGF-1 NPs is able to extend Akt phosphorylation for a longer time than the treatment with IGF-1 alone.

Example 5

IGF-1 and PLGA-IGF-1 NPs of the Present Invention Prevent Cardiomyocyte Apoptosis In Vitro Cardiomyocytes were isolated and cultured the same as in Example 4. Cardiomyocytes were plated at a density of $5 \times 10^5$ cells/cm$^2$ in culture dishes overnight, cultured in serum-free DMEM for 24 hours, and then treated with IGF-1, PLGA NPs or PLGA-IGF-1 NPs for 1 hour. The negative control was not treated with IGF-1 or NPs. After the treatment, 1 μM doxorubicin (Sigma) was added to induce cardiomyocyte apoptosis for another 24 hours. The doxorubicin treated cells were collected by centrifugation and incubated in 0.1% Triton X-100 solution comprising 20 μM RNase (Sigma) at 37° C. for 30 minutes, then stained with 0.1 mg/mL propidium iodide (Sigma) for 10 minutes. After that, the cells were subjected to flow cytometry analysis by FACSCalibur.

Figure 6A:
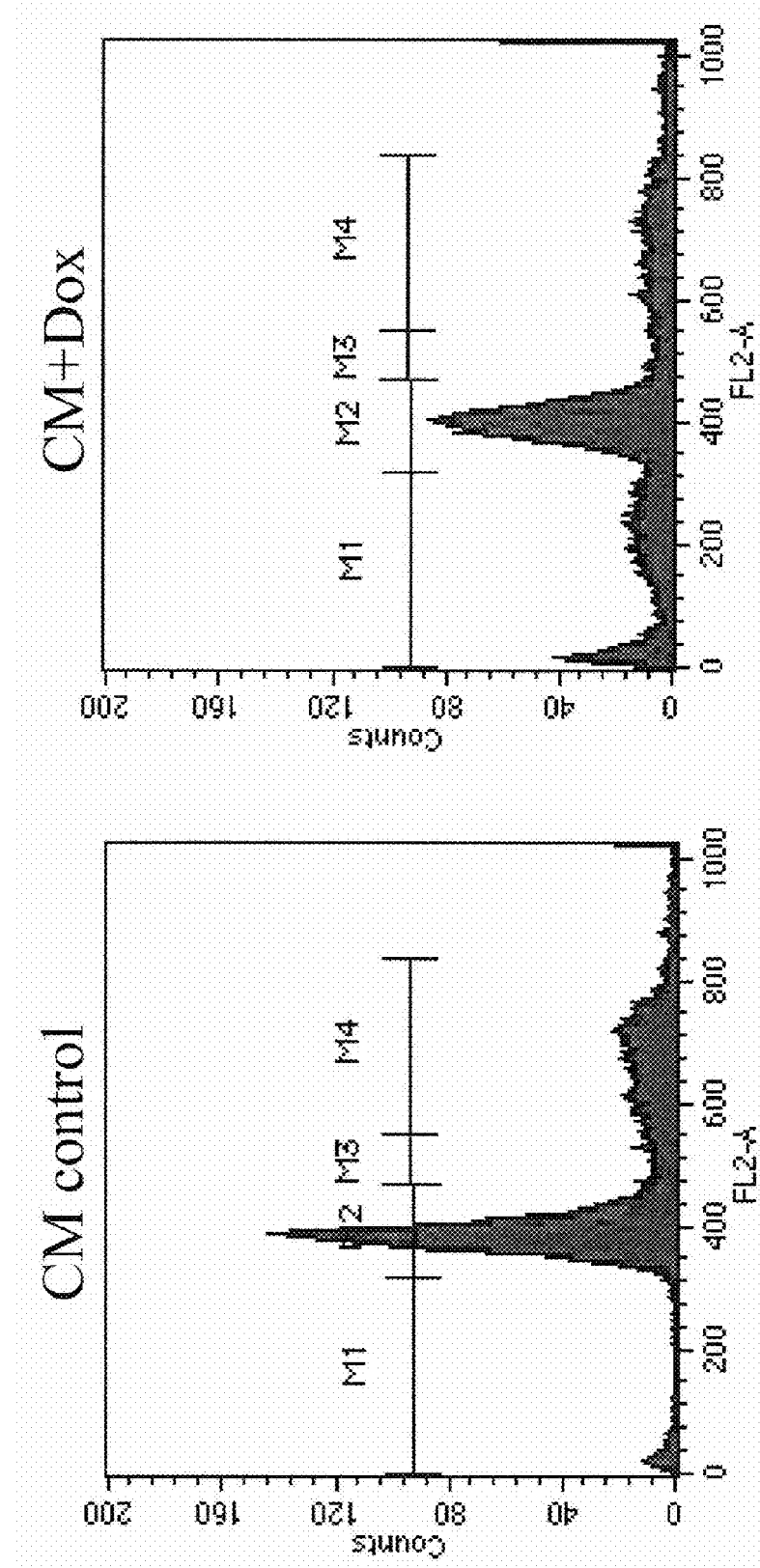
FIG. 6 represents (a) the flow cytometry result of doxorubicin-treated cardiomyocytes (Dox) and the Dox-treated cardiomyocytes further treated with PLGA NPs (PLGA NP+Dox), IGF-1 (IGF-1+Dox) or PLGA-IGF-1 NPs (PLGA-IGF-1+Dox) and (b) the normalized chart diagram thereof. : $P<0.01$. *: $P<0.001$.
Figure 6A:
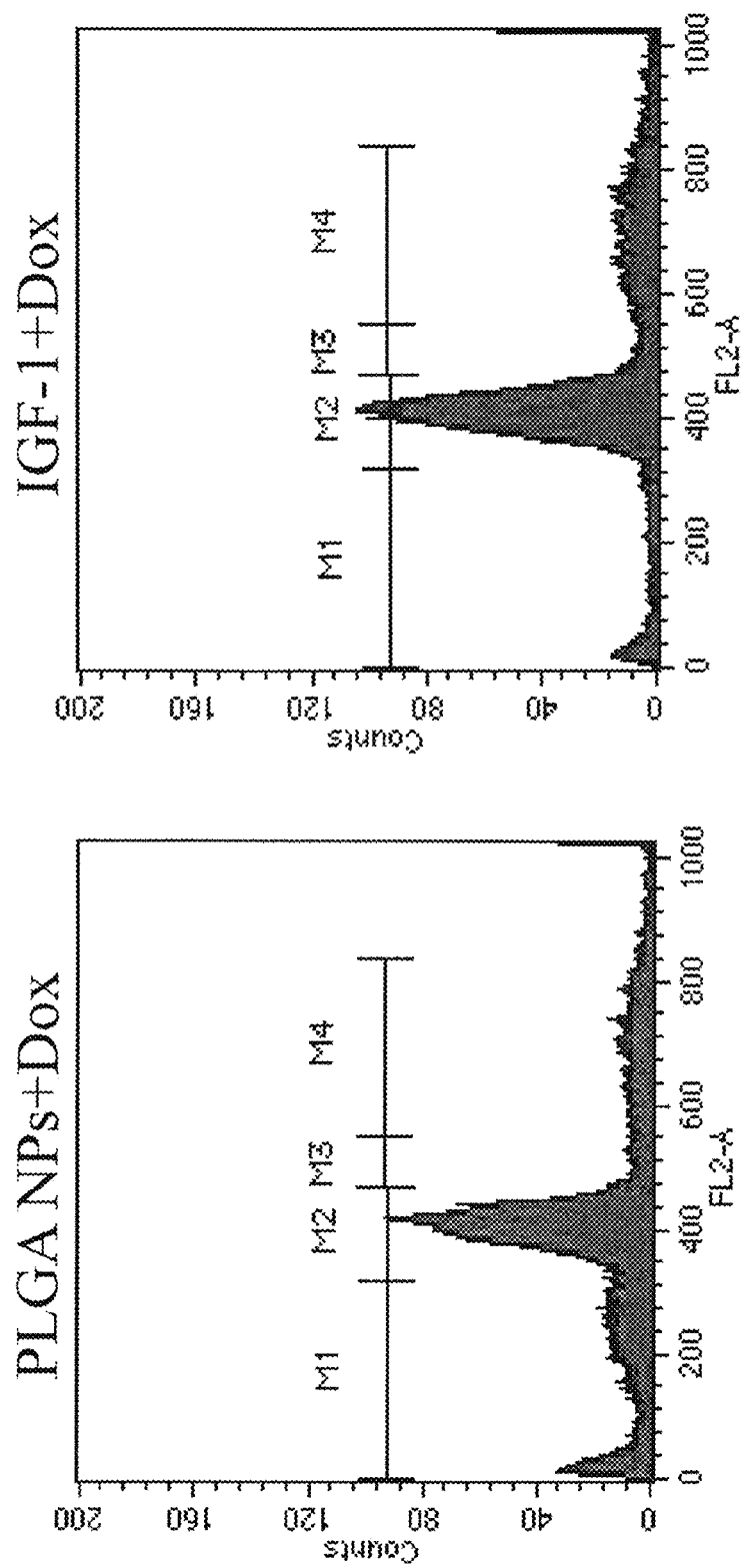
Figure 6A:
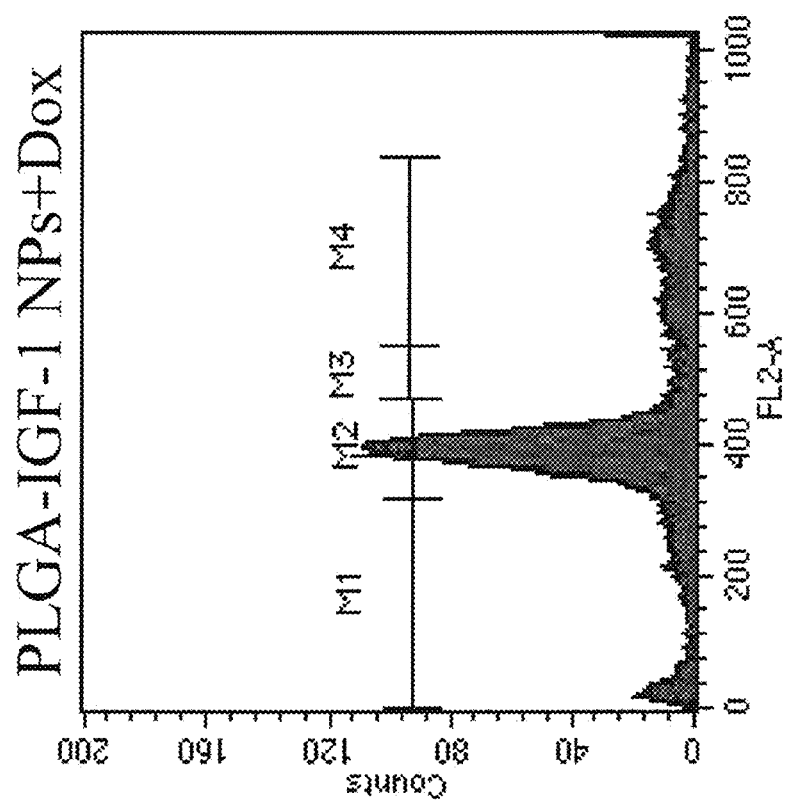
Figure 6B:
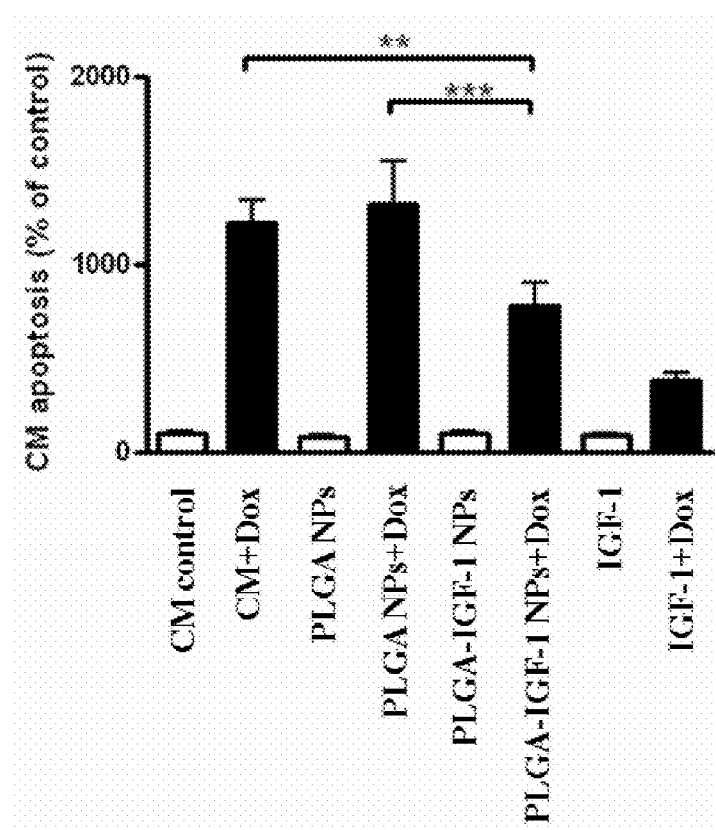

FIG. 6a shows the flow cytometry determination of apoptosis and FIG. 6b represents the normalized chart diagram of the flow cytometry data. Comparing to the control (CM+Dox) and PLGA NPs+Dox, IGF-1+Dox and PLGA-IGF-1 NPs+Dox significantly decrease cardiomyocyte apoptosis. In other words, the treatment with IGF-1 or PLGA-IGF-1 NPs protects cardiomyocytes from apoptosis.

Example 6

Figure 7:
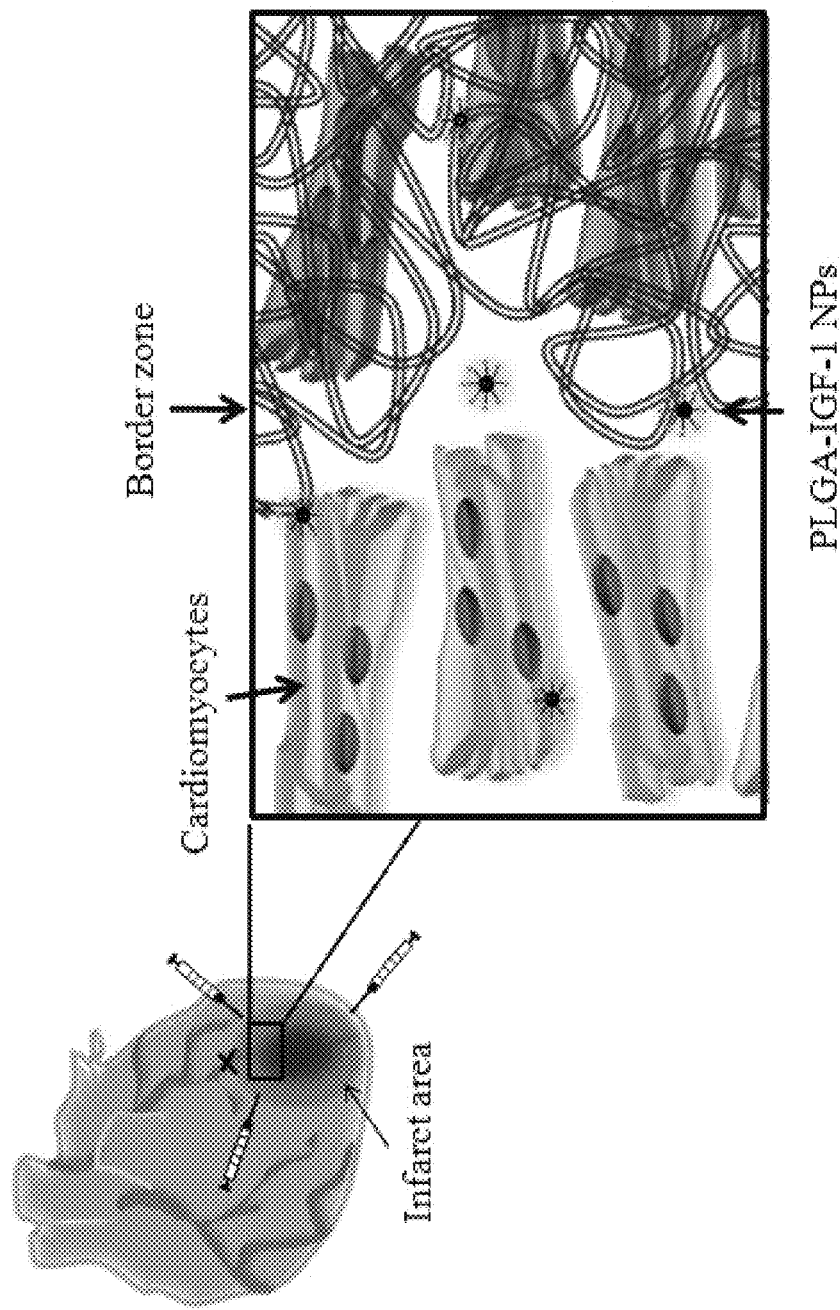
FIG. 7 is the schematic illustration of the PLGA-IGF-1 NP injection in the border zone via 3 different directions after induction of myocardial infarction.

PLGA-IGF-1 NPs of the Present Invention Prolongs Myocardial IGF-1 Retention In Vivo Male FVB mice weighted approximately 25 g were used for the following myocardial infarction experiments. First, mice were anesthetized by Zoletil-50 and 2% Rompun. After tracheal intubation and left thoracotomy, the mouse heart was exposed. Then the left coronary artery was identified after pericardiotomy and was ligated by suturing with 6-0 prolene at the location ~2-3 mm below the left artial appendix to induce myocardial infarction (MI). For the sham operation, suturing was performed without ligation. A total of 20 μL of PLGA NPs, PLGA-IGF-1 NPs (1 μg of IGF-1 was comprised) or IGF-1 alone (1 μg) was injected into the infracted border zone of the myocardium through 3 directions (equal amount for each injection) immediately after coronary artery ligation, as shown in FIG. 7. Mice injected with PLGA NPs were served as negative control. Following injection, the chest of the mice was closed and the animals were allowed to recover under a heating pad. All of the procedures were performed in a blinded and randomized manner. At least 5 animals were analyzed in each group.

Figure 8:
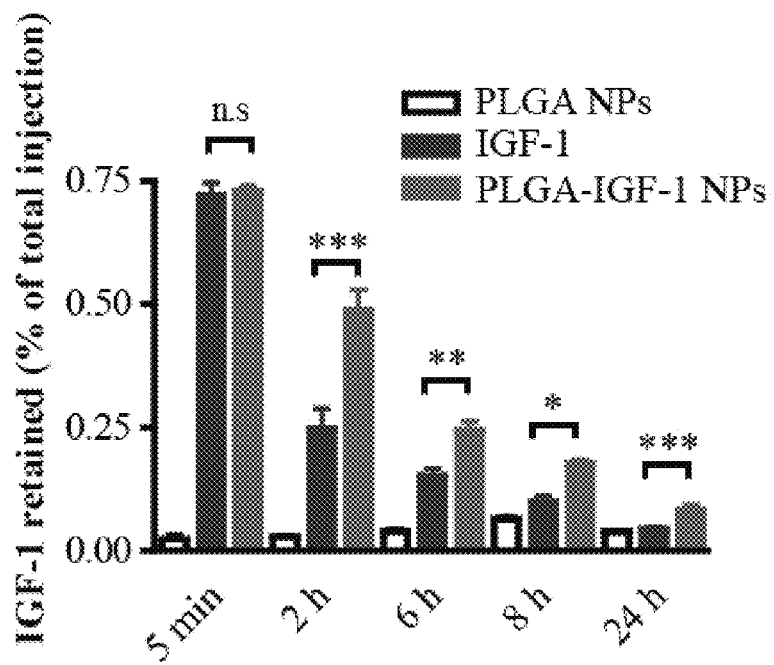
FIG. 8 represents (a) the retention of IGF-1 of mice injected with PLGA NPs, IGF-1 or PLGA-IGF-1 NPs within 24 hr and (b) Akt phosphorylation in the heart tissue from the mice injected with PBS, PLGA NPs, IGF-1 or PLGA-IGF-1 NPs one day after myocardial infarction. Sham indicates sham operation. *: $P<0.05$. ***: $P<0.001$. n.s.: no significant.
Figure 8:
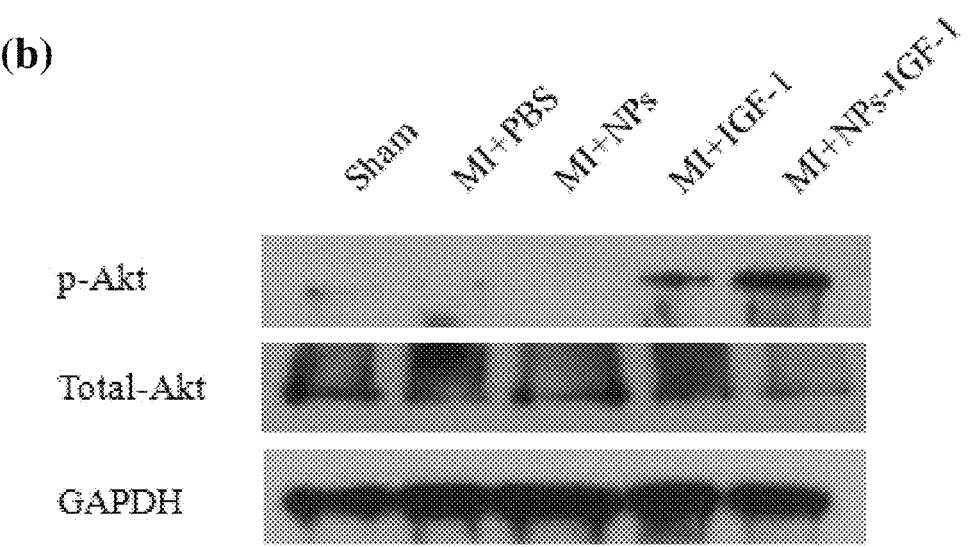

Protein samples were prepared from the heart tissues of the injection region by using a RIPA buffer containing 0.1% SDS, 10 mM Tris-Cl (pH 6.8), 120 mM NaCl, 1% NP-40, 1% deoxycholate and proteinase inhibitor cocktail (Sigma) at 1:100 dilution. Each protein sample was subjected to anti-human IGF-1 ELISA (Diagnostic Systems Laboratories, Webster) in triplicate following the manufacturer's instructions to determine the time during which IGF-1 was retained in the heart. As shown in FIG. 8a, the IGF-1 concentrations of the IGF-1 group and the PLGA-IGF-1 NPs group are almost the same in five minutes; however, the IGF-1 concentration in the heart of PLGA-IGF-1 NPs group is higher than the other groups in 2, 8 and 24 hours after injection. In other words, PLGA-IGF-1 NPs contribute to prolong IGF-1 retention in the heart up to 24 hours after injection.

Example 7

PLGA-IGF-1 NPs of the Present Invention Induces Myocardial Akt Phosphorylation In Vivo Western blotting was applied as Example 4 to examine the protein extracted from the injected regions 1 day after injection. FIG. 8b indicates that PLGA-IGF-1 NPs are able to prolong the retention of IGF-1 in the injected regions, which results in Akt phosphorylation in the myocardium, and the phosphorylated Akt of MI+PLGA-IGF-1 NPs has a much higher level than that in the other groups.

Figure 9:
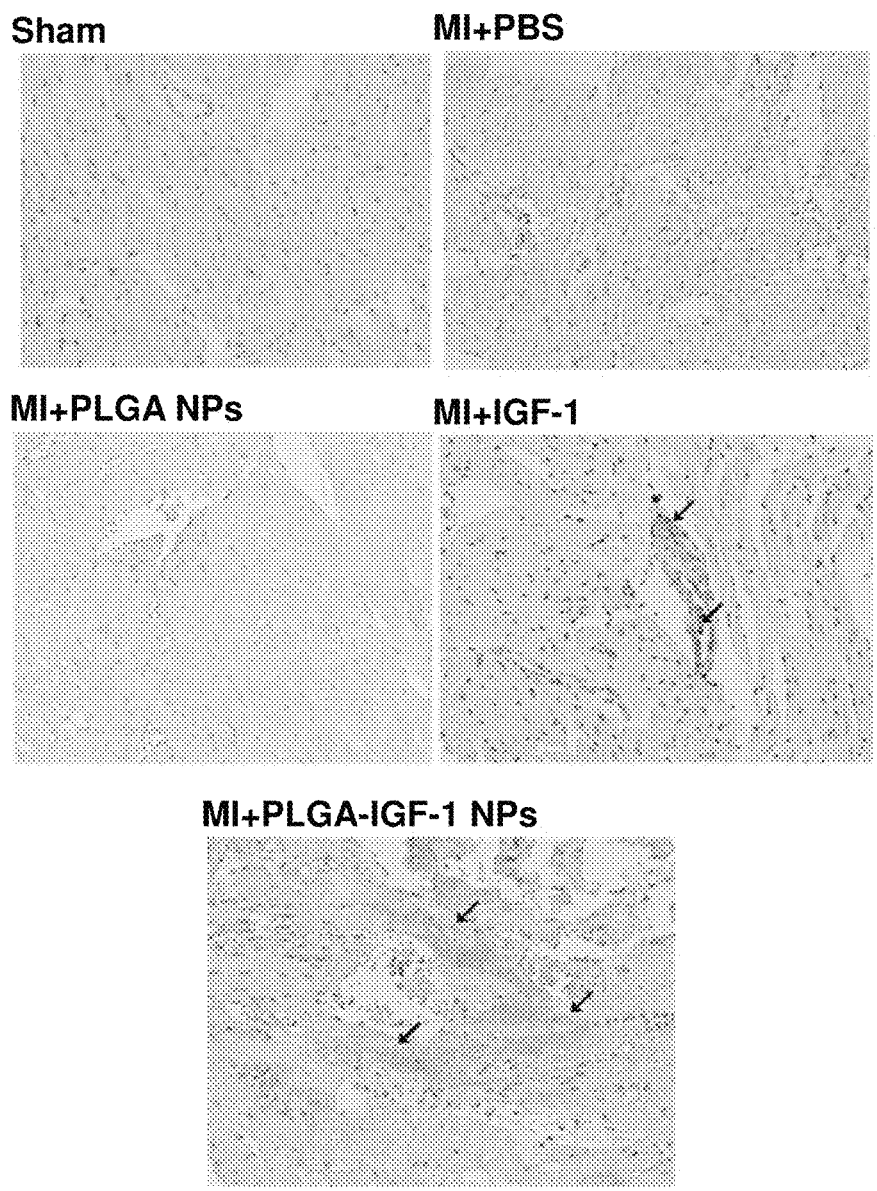
FIG. 9 represents the immunohistochemistry result of the mice injected with PBS, PLGA NPs, IGF-1 or PLGA-IGF-1 NPs one day after myocardial infarction. Arrows indicate phosphorylated Akt (brown) (200×). Sham indicates sham operation.

In addition, immunohistochemistry was used to measure the infarct size. First, mouse hearts were harvested and fixed with 4% paraformaldehyde at 4° C. overnight, then stored in 70% ethanol for further use. After samples were collected, these fixed heart samples were embedded by paraffin and sliced into histological sections. After that, the heart sections were de-paraffinized, rehydrated and pre-treated with boiling 10 mM sodium citrate buffer (pH 6.0) for 10 minutes. The pre-treated sections were incubated in 3% $H_2O_2$ at room temperature for 10 minutes and washed with PBS-T for 3 times. Then the heart sections were blocked with 1% BSA containing 5% FBS and 5% goat serum in PBS-T at room temperature for 1 hour. After blocking, the sections were probed with the following primary antibodies at 4° C. overnight: anti-human rhIGF-1, cleaved caspase-3 and anti-phospho-Akt (Cell Signaling) Primary antibodies were removed by washing with PBS-T for 3 times, each for 5 minutes. Corresponding secondary antibodies were used and incubated at room temperature for 30 minutes, and then washed with PBS-T for 3 times. As shown in FIG. 9, the arrows indicate staining positive for phosphor-Akt (brown) (200×).

Example 8

Cardioprotection Effect of PLGA-IGF-1 NPs of the Present Invention

All tests were performed in blinded and randomized ways. A total of 57 male FVB mice weighted approximately 25 g were used to study the cardioprotection effect of PLGA-IGF-1 NPs of the present invention, and at least ten animals were used in each group (n=10 in Sham group, n=13 in MI+PBS group, n=12 in MI+NPs group, n=10 in MI+IGF-1 group and n=12 in MI+PLGA-IGF-1 NPs group).

One or twenty-one days after myocardial infarction, echocardiographic acquisition and analysis were performed by an in vivo micro imaging system (Vevo 770, Visualsonics, Toronto, Canada). End-diastolic dimension (EDD, mm), end-systolic dimension (ESD, mm) and ejection fraction (EF) at the papillary muscle level of the left ventricle were measured, and left ventricular fractional shortening demonstrated by EF % was calculated by the following formula:

$$EF\% = \frac{(EDD - ESD)}{EDD} \times 100\%$$

From the result shown in Table 2, it should be clear that the elevated level of EDD and ESD by PLGA-IGF-1 NPs of the present invention is less than those in IGF-1 and PLGA NPs and closer to that in the sham control. That is to say, the treatment with PLGA-IGF-1 NPs of the present invention prevents myocardial dilation after myocardial infarction.

TABLE 2

End-diastolic and end-systolic dimension by echocardiography 1 and 21 days after infarction

|  |  | Sham | MI | MI + PLGA NPs | MI + IGF-1 | MI + PLGA-IGF-1 NPs |
|---|---|---|---|---|---|---|
|  | n | 10 | 13 | 11 | 10 | 10 |
| 1 d | EDD | 3.47 ± 0.29 | 3.87 ± 0.31 | 3.68 ± 0.28 | 3.79 ± 0.34 | 3.57 ± 0.38 |
|  | ESD | 2.40 ± 0.39 | 2.96 ± 0.26 | 2.90 ± 0.33 | 2.88 ± 0.37 | 2.60 ± 0.36 |
| 21 d | EDD | 3.79 ± 0.20 | 4.61 ± 0.56 | 4.72 ± 0.80 | 4.85 ± 0.49 | 4.21 ± 0.25 [A] |
|  | ESD | 2.71 ± 0.19 | 3.72 ± 0.62 | 3.70 ± 0.96 | 3.87 ± 0.58 | 3.11 ± 0.30 [B] |

EDD, end-diastolic dimension; ESD, end-systolic dimension.
[A] $P < 0.05$ compared with MI + IGF-1
[B] $P < 0.05$ compared with MI, MI + PLGA NPs and MI + IGF-1

Figure 10:
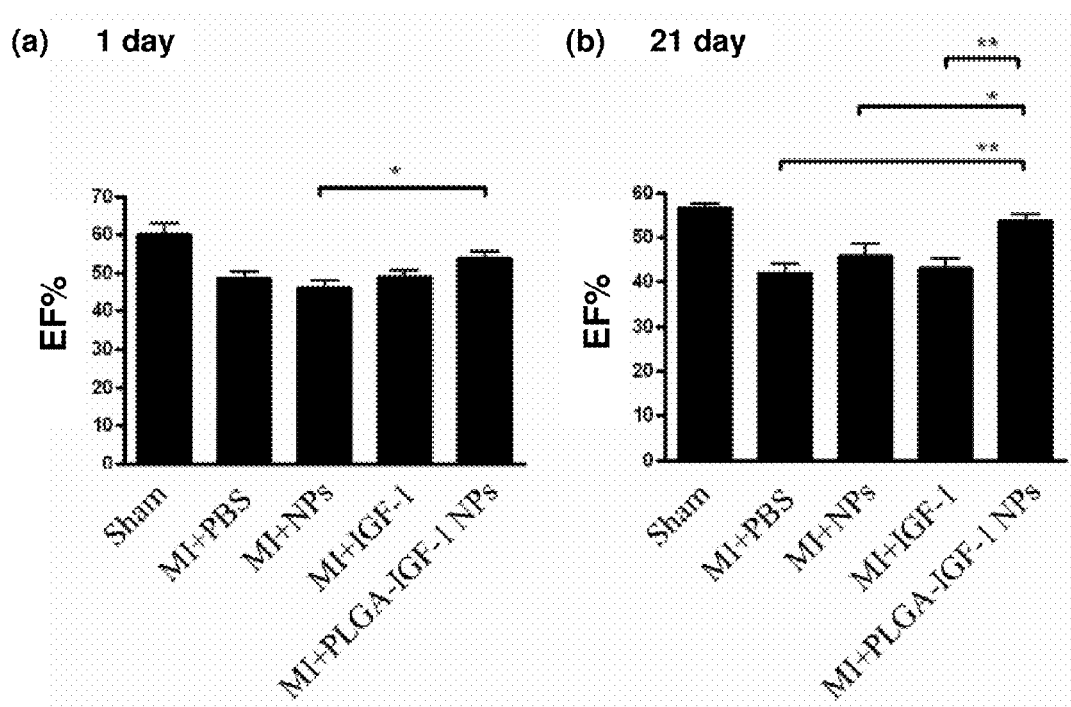
FIG. 10 represents the left ventricular ejection fraction % (EF %) of the sham mice and the mice injected with PBS, PLGA NP, IGF-1 or PLGA-IGF-1 NP (a) 1 day or (b) 21 days after myocardial infarction by echocardiography. *: $P<0.05$. **: $P<0.01$.

FIGS. 10a and 10b represent the left ventricular ejection fraction (EF %) of the mice injected with PBS, PLGANPs, IGF-1 alone or PLGA-IGF-1 NPs at 1 day and 21 days after myocardial infarction, respectively. As shown in FIG. 10a, the ejection fraction of the MI+PLGA-IGF-1 NPs group was obviously higher than that in the MI+PLGA NPs group, and there was no difference between all the other groups (59.9%±9.1% in sham, 48.7%±5.9 in MI+PBS, 46.9%+5.9% in MI+PLGA NPs, 48.9%±6.0% in MI+IGF-1 and 52.6%±6.9% in MI+PLGA-IGF-1 NPs), indicating a similar baseline of cardiac injury after surgery. Twenty-one days later, however, significant improvement of ejection fraction was observed in the animals injected with PLGA-IGF-1 NPs (55.8%=3.4% in sham, 42.0%±6.8 in MI+PBS, 45.8%±9.9% in MI+PLGA NPs, 43.1%±6.8% in MI+IGF-1 and 52.5%±7.4% in MI+PLGA-IGF-1 NPs), as shown in FIG. 10b.

Furthermore, Masson's trichrome staining was used to detect the infarcted scar size at 21 days after myocardial infarction. The infarcted area, i.e. fibrotic heart tissue after ischemia, cannot contract as normal cardiac muscle, and results in ventricular dilation, and ultimately, heart failure.

First, left ventricles of all mice were harvested and fixed with 4% paraformaldehyde at 4° C. overnight and stored in 70% ethanol. After samples were collected, these ventricle samples were embedded in paraffin, sliced into histological sections, and subjected to Masson's trichrome staining. The size of infarcted and non-infracted areas were measured by automated computer image analysis, and the ratio of infarcted to non-infarcted area of the left ventricles of mouse heart was calculated by the following formula:

$$\text{Infract area (\%)} = \frac{\text{infracted area}}{\left(\begin{array}{c}\text{the volume of left ventricle} - \\ \text{the volume of left ventricle chamber}\end{array}\right)}$$

Figure 11:
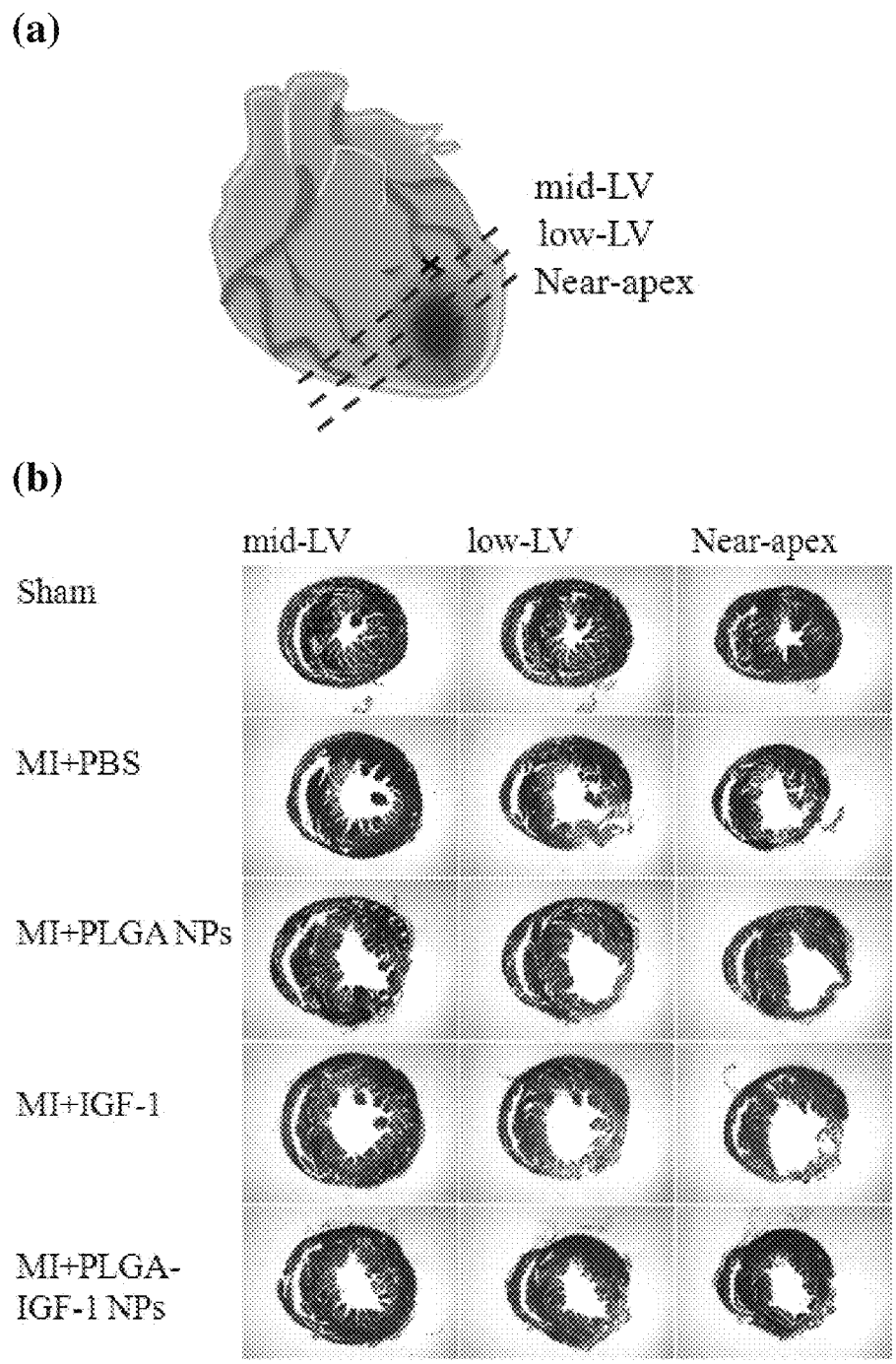
FIG. 11 represents (a) the schematic illustration of the area of cross-sections from which the infarct size was determined, and (b) the Masson tri-chrome staining of heart sections from sham mice and the mice injected with PBS, PLGA NPs, IGF-1 or PLGA-IGF-1 NPs of the present invention 21 days after myocardial infarction.
Figure 12:
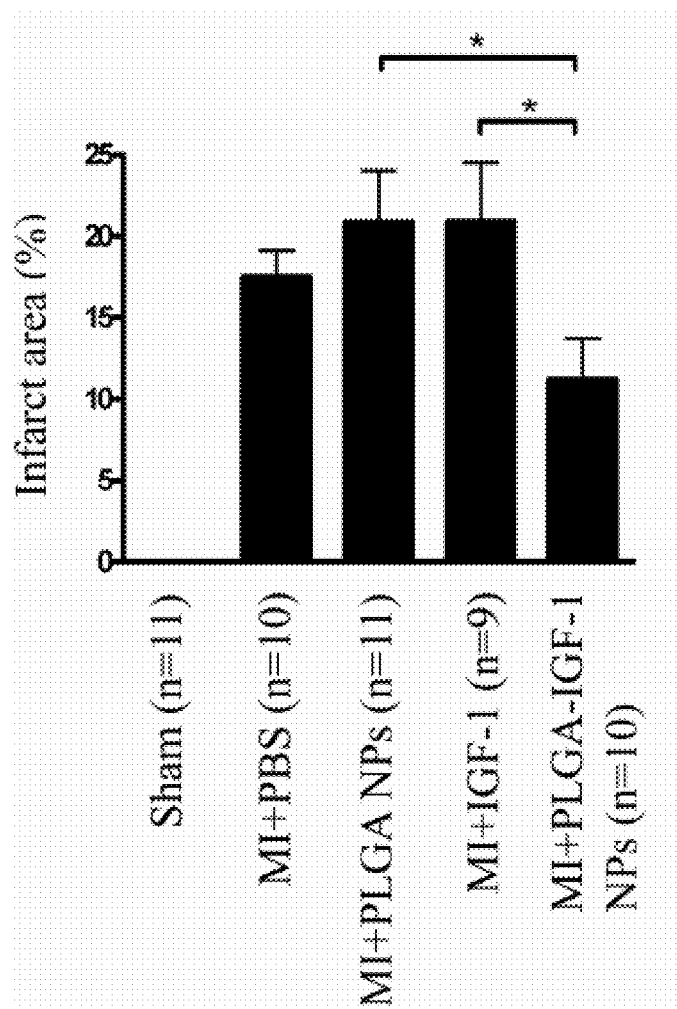
FIG. 12 represents the infarct size of sham mice and the mice injected with PBS, PLGA NPs, IGF-1 or PLGA-IGF-1 NPs of the present invention 21 days after myocardial infarction. *: $P<0.05$.

There were at least 8 animals from each group in this study. The data shown in FIG. 11 represents that the infarct size of the heart which received injection of PLGA-IGF-1 NPs of the present invention was significantly reduced than that in the other groups receiving injection of PLGA-NPs or IGF-1 alone. FIG. 12 represents the reduction of the infarct size of all groups of mice. FIGS. 11 and 12 show that injection of PLGA-IGF-1 NPs of the present invention can reduce the infarct size, which means improved contracting myocardial mass.

In summary, the type of PLGA-IGF-1 NPs of the present invention has the ability to prolong cardioprotection and improve cardiac functions after acute infarction when they are injected into the peri-infarct area. Therefore, the PLGA-IGF-1 NPs of the present invention have the potential to be used for treating cardiovascular diseases.

We claim:

1. A type of functionalized nanoparticles for drug delivery, comprising:
   a type of polymer nanoparticles, in which the polymer of said type of polymer nanoparticles is PLGA, collagen, gelatin, chitosan, chitin, hyaluronic acid, alginate, albumin, fibrin, agarose or cellulose;
   a single layer of polymer stabilizer coating, in which the polymer stabilizer is poly(ethylene)imine, polylysine or a polyamine material selected from the group of spermidine and putrescine; and
   a drug, which is a protein selected from a cytokine, a growth factor or a synthetic protein,
   wherein
   said polymer stabilizer coating is coated on the surface of said type of polymer nanoparticles,
   said drug is conjugated to said polymer stabilizer coating through an electrostatic interaction between the drug and the polymer stabilizer coating, and
   said nanoparticles have an average diameter of from 5 to 500 nm.

2. The type of functionalized nanoparticles according to claim 1, wherein said drug is IGF-1, PDGF, VEGF, HGF, G-CSF, FGF, BMP, SHH, periostin, neuregulin, a p38 inhibitor or a combination thereof.

3. The type of functionalized nanoparticles according to claim 1, which are administrated by injection.

4. A method for treating an ischemic disease or a degenerative disease, comprising administrating an effective amount of the type of functionalized nanoparticles according to claim 1 to a subject suffering from the ischemic disease or the degenerative disease.

5. The method according to claim 4, wherein said ischemic disease comprises ischemic stroke and peripheral arterial occlusive diseases.

6. The method according to claim 4, wherein said degenerative disease comprises neurological and musculoskeletal system disorders.

7. A type of functionalized nanoparticles for drug delivery, comprising:
   a type of polymer nanoparticles, in which the polymer of said type of polymer nanoparticles is PLGA;

a single layer of polymer stabilizer coating, in which the polymer stabilizer is poly(ethylene)imine, polylysine or a polyamine material selected from the group of spermidine and putrescine; and a drug, which is IGF-1, wherein said polymer stabilizer coating is coated on the surface of said type of polymer nanoparticles, said drug is conjugated to said polymer stabilizer coating, and said nanoparticles have an average diameter of from 5 to 500 nm.

8. A method for regenerating a cell, a tissue or an organ in a subject, comprising administering an effective amount of the type of functionalized nanoparticles according to claim 1 to a subject in need of regenerating the cell, the tissue or the organ.

* * * * *